(12) United States Patent
Mathias

(10) Patent No.: US 7,566,327 B2
(45) Date of Patent: Jul. 28, 2009

(54) NEEDLE PROTECTOR

(75) Inventor: Jean-Marie Mathias, Lillois (BE)

(73) Assignee: Fenwal, Inc., Lake Zurich, IL (US)

( * ) Notice: Subject to any disclaimer, the term of this patent is extended or adjusted under 35 U.S.C. 154(b) by 294 days.

(21) Appl. No.: 10/618,353

(22) Filed: Jul. 11, 2003

(65) Prior Publication Data
US 2005/0049559 A1 Mar. 3, 2005

Related U.S. Application Data

(60) Provisional application No. 60/402,286, filed on Aug. 9, 2002.

(51) Int. Cl.
*A61M 5/00* (2006.01)
*A61M 5/32* (2006.01)

(52) U.S. Cl. ..................... 604/263; 604/192

(58) Field of Classification Search ............... 604/180, 604/192, 158, 159, 162, 198, 171, 263, 164.01, 604/164.04, 164.07, 164.08, 110
See application file for complete search history.

(56) References Cited

U.S. PATENT DOCUMENTS

| | | |
|---|---|---|
| 2,857,912 A | 10/1958 | Feinstone et al. |
| 3,323,523 A | 6/1967 | Scislowicz et al. |
| 3,568,673 A | 3/1971 | Cowley |
| 3,572,334 A | 3/1971 | Petterson |
| 3,595,230 A | 7/1971 | Suyeoka et al. |
| 3,610,240 A | 10/1971 | Harautuneian |
| RE27,797 E | 10/1973 | Sorenson et al. |
| 3,910,272 A | 10/1975 | Forberg |
| 4,068,659 A | 1/1978 | Moorehead |
| 4,170,993 A | 10/1979 | Alvarez |
| 4,329,989 A | 5/1982 | Dallons et al. |
| 4,417,887 A | 11/1983 | Koshi |
| 4,425,120 A | 1/1984 | Sampson et al. |
| 4,573,976 A | 3/1986 | Sampson et al. |
| 4,631,057 A | 12/1986 | Mitchell |
| 4,631,058 A | 12/1986 | Raines |
| 4,643,722 A | 2/1987 | Smith, Jr. |
| 4,664,654 A | 5/1987 | Strauss |
| 4,676,783 A | 6/1987 | Jagger et al. |
| 4,693,708 A | 9/1987 | Wanderer et al. |

(Continued)

FOREIGN PATENT DOCUMENTS

CA 729419 3/1966

(Continued)

OTHER PUBLICATIONS

Compact Oxford English Dictionary definition of "profile." http://www.askoxford.com/concise_oed/profile?view=uk.*

(Continued)

*Primary Examiner*—Kevin C Sirmons
*Assistant Examiner*—Catherine N Witczak
(74) *Attorney, Agent, or Firm*—Cook Alex Ltd.

(57) ABSTRACT

Needle protectors for housing used blood collection needles are disclosed. The needle protectors are single-piece protectors that include an open distal end for receiving a needle hub (with needle mounted thereon). A retaining member locks the hub when the needle hub is fully retracted. A viewing slot in one of the walls of the needle protector is provided.

19 Claims, 4 Drawing Sheets

U.S. PATENT DOCUMENTS

| | | | |
|---|---|---|---|
| 4,731,059 A | 3/1988 | Wanderer et al. | |
| 4,735,618 A | 4/1988 | Hagen | |
| 4,737,143 A | 4/1988 | Russell | |
| 4,747,836 A | 5/1988 | Luther | |
| 4,790,828 A | 12/1988 | Dombrowski et al. | |
| 4,820,282 A | 4/1989 | Hogan | |
| 4,840,613 A | 6/1989 | Balbierz | |
| 4,840,619 A | 6/1989 | Hughes | |
| 4,842,587 A | 6/1989 | Poncy | |
| 4,867,172 A | 9/1989 | Haber et al. | |
| 4,874,383 A | 10/1989 | McNaughton | |
| 4,888,001 A | 12/1989 | Schoenberg | |
| 4,917,243 A | 4/1990 | Abrams et al. | |
| 4,923,445 A | 5/1990 | Ryan | |
| 4,927,019 A | 5/1990 | Haber et al. | |
| 4,927,415 A | 5/1990 | Brodsky | |
| 4,929,241 A | 5/1990 | Kulli | |
| 4,932,940 A | 6/1990 | Walker et al. | |
| 4,935,011 A | 6/1990 | Hogan | |
| 4,935,012 A | 6/1990 | Magre et al. | |
| 4,941,881 A | 7/1990 | Masters et al. | |
| 4,943,283 A | 7/1990 | Hogan | |
| 4,943,284 A | 7/1990 | Erlich | |
| 4,946,447 A | 8/1990 | Hardcastle et al. | |
| 4,994,046 A | 2/1991 | Wesson et al. | |
| 5,013,305 A | 5/1991 | Opie et al. | |
| 5,030,212 A | 7/1991 | Rose | |
| 5,061,250 A | 10/1991 | Shields | |
| 5,067,490 A | 11/1991 | Haber | |
| 5,069,341 A | 12/1991 | Barbieri et al. | |
| 5,085,639 A | 2/1992 | Ryan | |
| 5,086,780 A | 2/1992 | Schmitt | |
| 5,088,982 A | 2/1992 | Ryan | |
| 5,092,461 A | 3/1992 | Adam | |
| 5,098,403 A | 3/1992 | Sampson | |
| 5,108,376 A | 4/1992 | Bonaldo | |
| 5,112,311 A | 5/1992 | Utterberg et al. | |
| 5,112,313 A | 5/1992 | Sallee | |
| 5,120,320 A | 6/1992 | Fayngold | |
| 5,137,515 A | 8/1992 | Hogan | |
| 5,137,519 A | 8/1992 | Littrell et al. | |
| 5,154,698 A | 10/1992 | Compagnucci et al. | |
| 5,167,640 A | 12/1992 | Balding | |
| 5,169,392 A | 12/1992 | Ranford et al. | |
| 5,171,231 A | 12/1992 | Heiliger | |
| 5,176,650 A | 1/1993 | Haining | |
| 5,188,119 A | 2/1993 | Sunderland | |
| 5,192,275 A | 3/1993 | Burns | |
| 5,197,956 A | 3/1993 | Brizuela | |
| RE34,223 E | 4/1993 | Bonaldo | |
| 5,201,713 A | 4/1993 | Rossetti | |
| 5,215,528 A | 6/1993 | Purdy et al. | |
| 5,219,339 A | 6/1993 | Saito | |
| 5,226,894 A | 7/1993 | Haber et al. | |
| 5,242,417 A | 9/1993 | Paudler | |
| 5,266,072 A | 11/1993 | Utterberg et al. | |
| 5,279,588 A | 1/1994 | Nicoletti et al. | |
| 5,290,264 A | 3/1994 | Utterberg | |
| 5,312,359 A | 5/1994 | Wallace | |
| 5,312,368 A | 5/1994 | Haynes | |
| 5,330,438 A | 7/1994 | Gollobin et al. | |
| 5,346,475 A | 9/1994 | Gregorio | |
| 5,350,368 A | 9/1994 | Shields | |
| D353,456 S | 12/1994 | Fayngold et al. | |
| 5,376,075 A | 12/1994 | Haughton et al. | |
| 5,380,293 A | 1/1995 | Grant | |
| 5,382,240 A | 1/1995 | Lam | |
| 5,401,250 A | 3/1995 | Shields | |
| 5,425,720 A | 6/1995 | Rogalsky et al. | |
| 5,429,612 A | 7/1995 | Berthier | |
| 5,429,613 A | 7/1995 | D'Amico | |
| 5,433,703 A | 7/1995 | Utterberg et al. | |
| 5,486,163 A | 1/1996 | Haynes | |
| 5,495,855 A | 3/1996 | Dudar et al. | |
| 5,498,241 A | 3/1996 | Fabozzi | |
| 5,498,244 A | 3/1996 | Eck | |
| 5,498,245 A | 3/1996 | Whisson | |
| 5,501,672 A | 3/1996 | Firth et al. | |
| 5,505,711 A | 4/1996 | Arakawa et al. | |
| 5,520,654 A | 5/1996 | Wahlberg | |
| 5,545,146 A | 8/1996 | Ishak | |
| 5,549,558 A | 8/1996 | Martin | |
| 5,549,571 A | 8/1996 | Sak | |
| 5,549,572 A | 8/1996 | Byrne et al. | |
| 5,554,130 A | 9/1996 | McDonald et al. | |
| 5,562,636 A | 10/1996 | Utterberg | |
| 5,562,637 A | 10/1996 | Utterberg | |
| 5,573,512 A | 11/1996 | Van den Haak | |
| 5,584,813 A | 12/1996 | Livingston et al. | |
| 5,601,536 A | 2/1997 | Crawford et al. | |
| 5,643,220 A | 7/1997 | Cosme | |
| 5,672,160 A * | 9/1997 | Osterlind et al. | 604/263 |
| 5,672,161 A | 9/1997 | Allen et al. | |
| 5,681,295 A | 10/1997 | Gyure et al. | |
| 5,693,022 A | 12/1997 | Haynes | |
| 5,704,917 A | 1/1998 | Utterberg | |
| 5,704,920 A | 1/1998 | Gyure et al. | |
| 5,704,924 A | 1/1998 | Utterberg et al. | |
| 5,718,688 A | 2/1998 | Wozencroft | |
| 5,735,827 A | 4/1998 | Adwers | |
| 5,746,215 A * | 5/1998 | Manjarrez | 600/573 |
| 5,746,718 A | 5/1998 | Steyn | |
| 5,749,859 A | 5/1998 | Powell | |
| 5,772,638 A | 6/1998 | Utterberg et al. | |
| 5,795,339 A | 8/1998 | Erskine | |
| 5,800,400 A | 9/1998 | Hogan | |
| 5,810,775 A | 9/1998 | Shaw | |
| 5,817,064 A | 10/1998 | DeMarco et al. | |
| 5,827,239 A | 10/1998 | Dillon et al. | |
| 5,833,670 A | 11/1998 | Dillon et al. | |
| 5,846,227 A | 12/1998 | Osterlind | |
| 5,851,196 A | 12/1998 | Arnett | |
| 5,879,337 A | 3/1999 | Kuracina et al. | |
| 5,891,098 A | 4/1999 | Huang | |
| 5,891,099 A | 4/1999 | Nakajima et al. | |
| 5,897,508 A | 4/1999 | Konrad | |
| 5,899,886 A | 5/1999 | Cosme | |
| 5,910,132 A | 6/1999 | Schultz | |
| 5,925,032 A | 7/1999 | Clements | |
| 5,951,523 A * | 9/1999 | Osterlind et al. | 604/192 |
| 5,951,529 A | 9/1999 | Utterberg | |
| 6,013,059 A | 1/2000 | Jacobs | |
| 6,042,570 A | 3/2000 | Bell et al. | |
| 6,093,170 A | 7/2000 | Hsu et al. | |
| 6,120,482 A | 9/2000 | Szabo | |
| 6,165,157 A * | 12/2000 | Dillon et al. | 604/263 |
| 6,193,694 B1 | 2/2001 | Bell | |
| 6,200,294 B1 | 3/2001 | Liu | |
| 6,235,005 B1 | 5/2001 | Chang et al. | |
| 6,235,006 B1 | 5/2001 | Dillon et al. | |
| 6,238,375 B1 | 5/2001 | Powell | |
| 6,287,278 B1 | 9/2001 | Woehr et al. | |
| 6,293,925 B1 | 9/2001 | Safabash et al. | |
| D449,687 S | 10/2001 | Hommann et al. | |
| 6,302,868 B1 | 10/2001 | Mohammad | |
| 6,309,376 B1 | 10/2001 | Alesi | |
| 6,319,233 B1 | 11/2001 | Jansen | |
| 6,325,781 B1 | 12/2001 | Takagi et al. | |
| 6,328,713 B1 | 12/2001 | Hollister | |
| 6,332,875 B2 | 12/2001 | Inkpen et al. | |
| 6,355,021 B1 | 3/2002 | Nielsen et al. | |
| 6,632,201 B1 | 10/2003 | Mathias et al. | |

| | | | | |
|---|---|---|---|---|
| 6,908,455 B2 * | 6/2005 | Hajianpour | | 604/266 |

FOREIGN PATENT DOCUMENTS

| | | |
|---|---|---|
| EP | 0 265 159 A2 | 4/1988 |
| EP | 0 353 916 A1 | 7/1990 |
| EP | 0 425 448 A2 | 2/1991 |
| EP | 0 459 953 A1 | 4/1991 |
| EP | 0 475 857 A1 | 3/1992 |
| EP | 0 664 139 B1 | 7/1995 |
| EP | 0 830 871 B1 | 3/1998 |
| EP | 0 978 465 A1 | 12/2002 |
| FR | 2 263 789 | 3/1974 |
| WO | WO 90/03196 | 4/1990 |
| WO | WO 92/11885 | 7/1992 |
| WO | WO 95/24232 | 9/1995 |
| WO | WO 99/12594 B1 | 9/1998 |
| WO | WO 98/58584 | 12/1998 |
| WO | WO 00/06225 | 2/2000 |
| WO | PCT/US00/30822 | 11/2000 |
| WO | WO/01/36025 | 5/2001 |
| WO | WO 01/36025 * | 5/2001 |

OTHER PUBLICATIONS

Abstract of Japanese Patent Application No. 63-036413 (JP 8836413), filed Feb. 18, 1988.

* cited by examiner

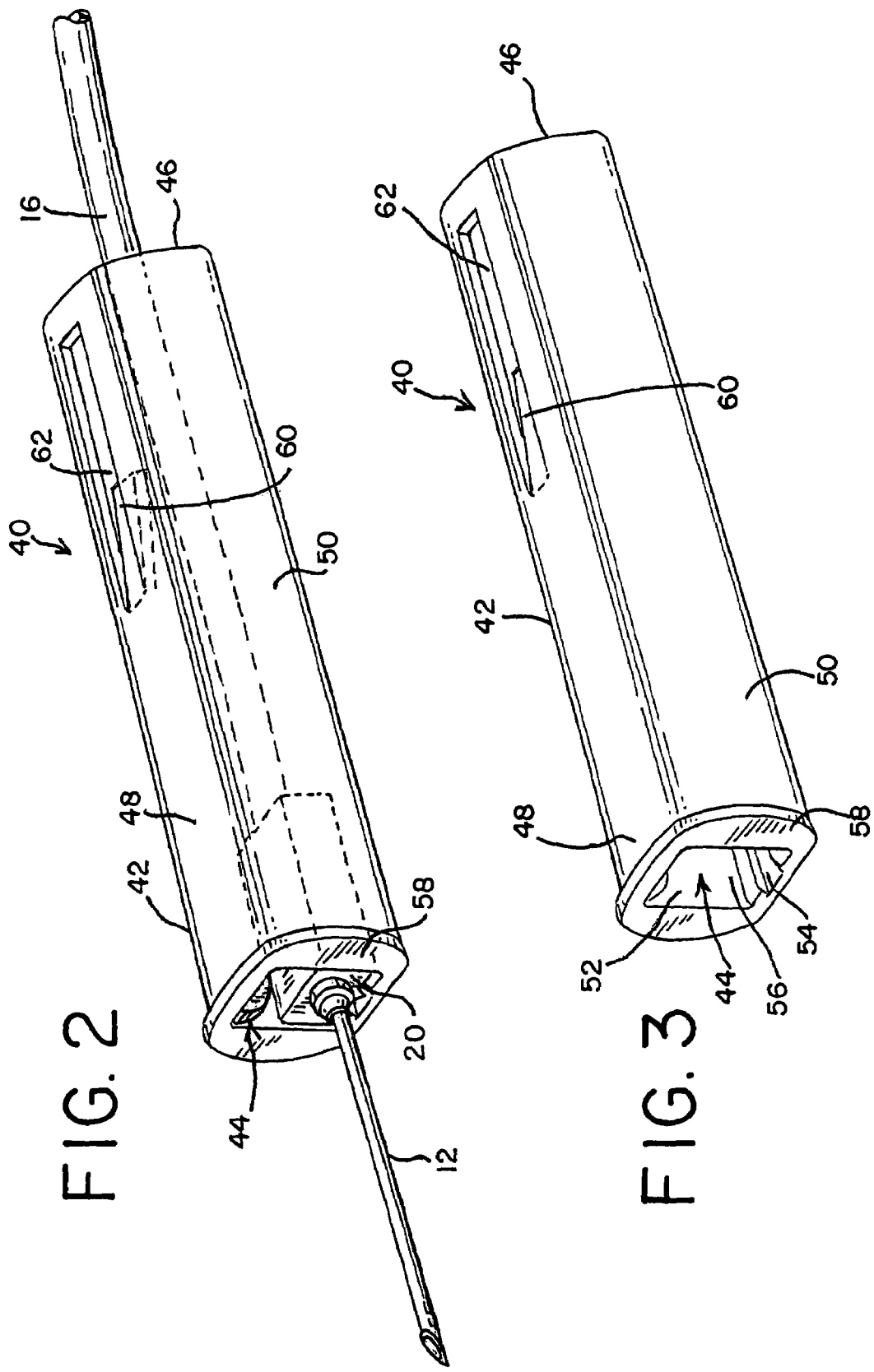

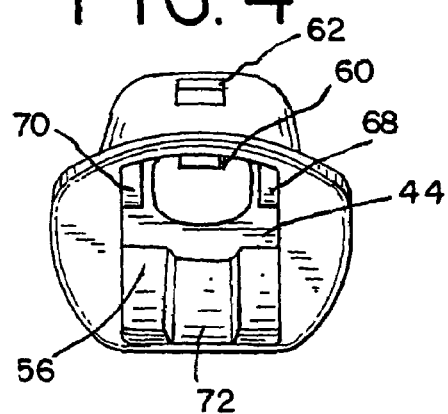
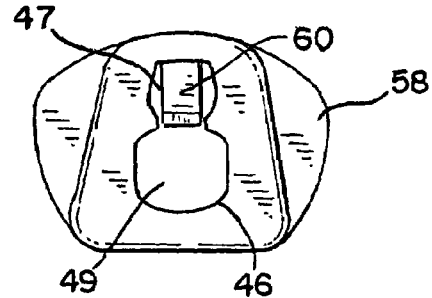
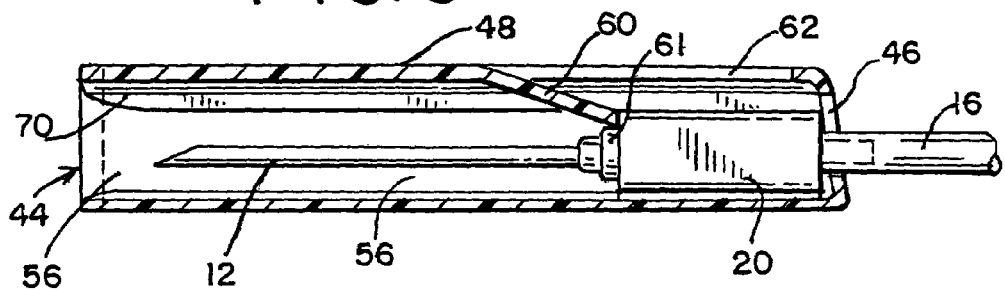
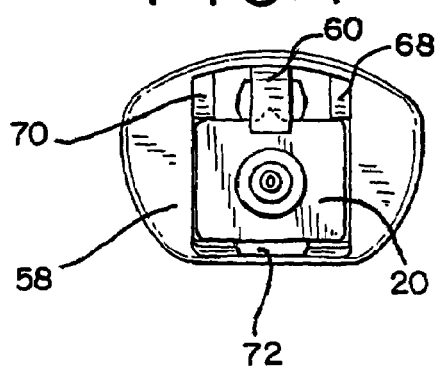
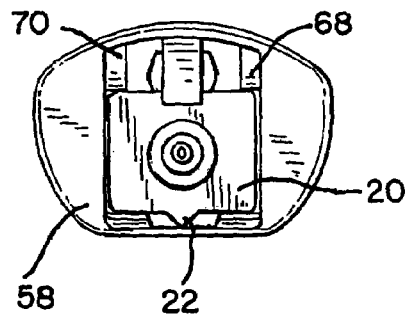

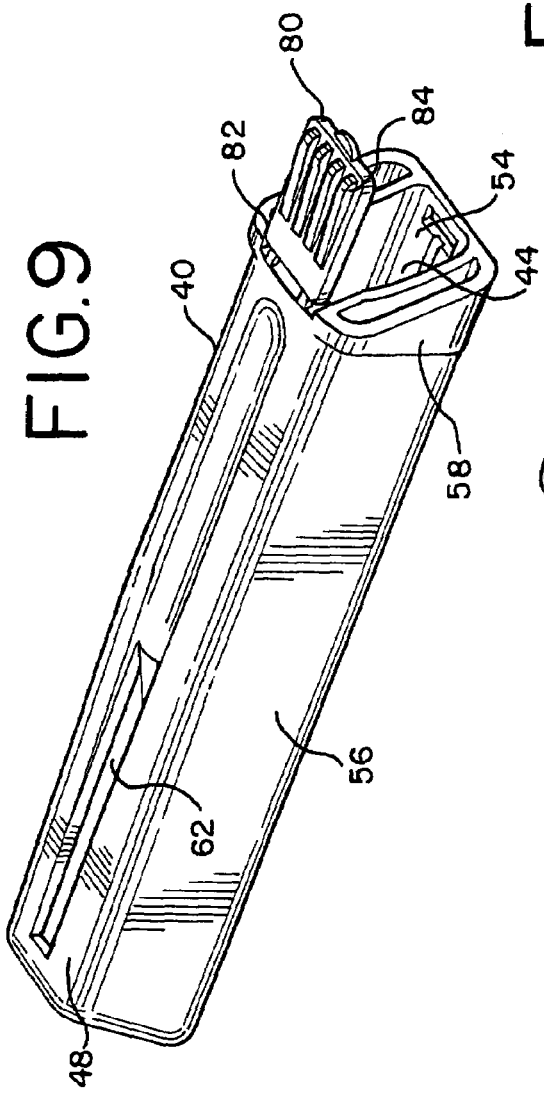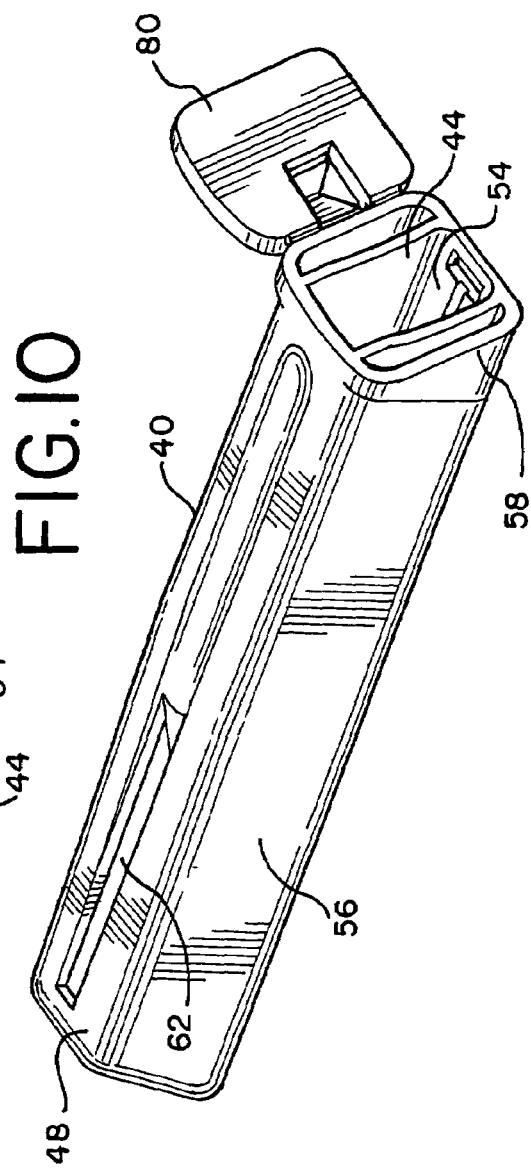

NEEDLE PROTECTOR

This application claims the benefit of U.S. Provisional Patent Application Ser. No. 60/402,286, filed Aug. 9, 2002.

The present invention relates generally to protective devices (i.e., needle protectors) for use with medical needles to prevent inadvertent user contact with such needles.

BACKGROUND OF THE INVENTION

Needle protectors are well known in the field of blood donation. Needle protectors are used to shield a used needle and, thereby, protect the medical personnel from an accidental needle stick. blood donation or collection kit, which includes a needle attached to one end of a needle hub. The other end of the need hub is attached to a length of plastic tubing that provides a flow path to one or more containers used to collect the donated blood. The needle protector is often provided as a sleeve placed around the plastic tube. The plastic tube extends through the needle protector, entering through one open end and exiting through an opposite open end.

After blood donation, the tube is pulled by the medical technician to retract the needle and needle hub into the needle protector. The used needle is, thus, shielded from the medical technician.

U.S. Pat. Nos. 5,800,400, 6,042,570, and 6,165,157 are just a few of the many examples of known needle protectors. The needle protectors disclosed therein, and in other U.S. patents, include features to provide protection of medical personnel from accidental needle sticks. The needle protectors may also include features which prevent movement of the needle during blood donation, which could cause discomfort to the donor.

For example, U.S. Pat. No. 6,165,157 describes a needle protector that includes restraining means which restrain movement of the needle hub when the needle is inserted in the arm of the donor. The needle protector also includes locking means to secure the used needle in a completely shielded position after use.

While needle protectors such as those described above in the aforementioned patents have worked satisfactorily, efforts continue to provide a needle protector that assures the safety of the medical technician, is easy for the technician to manipulate and/or operate, and provides maximum comfort to the donor. Efforts continue to provide a needle protector that achieves these ends and combines them in a needle protector that is also easy and inexpensive to manufacture and easy to use by the medical personnel.

SUMMARY OF THE INVENTION

In one aspect, the present invention is directed to a needle protector for use with a needle assembly that includes a piercing end, a hub, and a plastic tube attached to the hub. The needle protector includes a body including distal and proximal open ends. The needle protector further includes a plurality of side walls extending between the distal and proximal open ends, the side walls defining an interior chamber within the body. The distal open end of the needle protector is adapted to receive the hub of the needle assembly. The proximal open end has an end wall defining an aperture that is adapted so that the hub cannot pass through the proximal open end. The aperture is a multiple profile window in which the first profile is adapted to allow the tubing to slide through and the second profile is adapted to retain or hold the tubing. The aperture is completely enclosed by the end wall so that the tubing is contained within the aperture. One of the side walls includes a flexible retaining member adapted for contacting the hub so that when the hub is in the fully retracted position the piercing end is completely contained within the interior chamber. The needle protector also includes a side wall that defines an internal groove extending from the distal open end to the proximal open end.

In another aspect, the present invention is directed to a needle protector assembly that includes a needle assembly. The needle assembly includes a piercing end attached to a hub and a length of tubing attached to the opposite end of the hub. The body of the hub further includes a rib. The needle protector assembly includes a body including distal and proximal open ends. The needle protector further includes a plurality of side walls extending between the distal and proximal open ends, the side walls defining an interior chamber within the body. The distal open end of the needle protector assembly is adapted to receive the hub of the needle assembly. One of the side walls includes a flexible retaining member adapted for contacting the hub so that when the hub is in the fully retracted position the piercing end is completely contained within the interior chamber. The needle protector assembly also includes a side wall that defines an internal groove extending from the distal open end to the proximal open end. The proximal open end has an end wall defining an aperture that is adapted so that the hub cannot pass through the proximal open end. The aperture is a multiple profile window in which the first profile is adapted to allow the tubing to slide through and the second profile is adapted to retain or hold the tubing. The aperture is completely enclosed by the end wall so that the tubing is contained within the aperture.

In other more specific aspects, the present invention includes the above-described needle protector that further includes a needle protector wherein the side walls include first and second guiding ledges extending inwardly from the side walls. In another aspect, the needle protector includes an axial groove in one of the side walls.

In another aspect, the other second open end of the needle protector may include a multiple profile window adapted to slidably receive and secure the blood collection tube.

BRIEF DESCRIPTION OF THE DRAWINGS

FIG. 2 is a perspective view of the needle protector embodying the present invention in association with a needle assembly;

FIG. 3 is a perspective view of the needle protector embodying the present invention;

FIG. 4 is a front perspective view of the needle protector of FIG. 3;

FIG. 5 is a rear perspective view of the needle protector of FIG. 3;

FIG. 6 is a cross-sectional side view of the needle protector embodying the present invention in association with a needle assembly;

FIG. 7 is a front perspective view of the needle protector in combination with a needle assembly;

FIG. 8 is a front perspective view of the needle protector in combination with the needle assembly wherein the needle hub is rotated 180°;

FIG. 9 is a perspective view of one embodiment of the needle protector of the present invention including an end cap; and FIG. 10 is a perspective view of another embodiment of the needle protector of the present invention including an end cap.

DETAILED DESCRIPTION OF THE DRAWINGS

Figure 1:
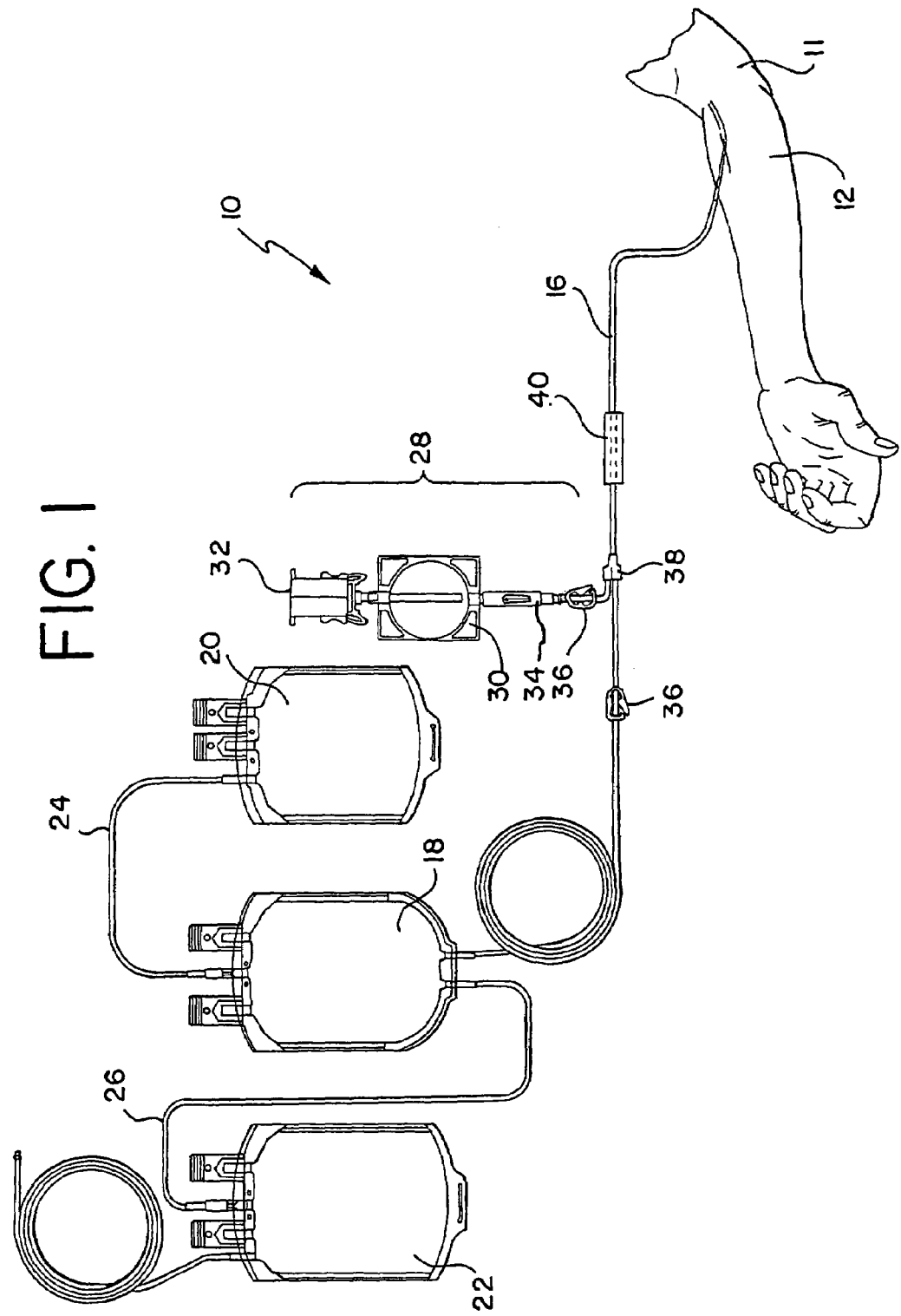
FIG. 1 is a plan view of a blood collection kit, including containers for collecting blood and a needle protector embodying the present invention.

The needle protector of the present invention will be described below in the context of its preferred use, namely, as a needle protector that is part of a disposable tubing and container set intended for the collection and processing of blood (or other biological fluid). It will be understood that the needle protector of the present invention is not limited to use with disposable tubing and container sets of the type shown in, for example, FIG. 1. In fact, the needle protector of the present invention may be used in any blood collection, donation, processing or treatment method and with any devices and tubing sets used for practicing such methods.

Also, as used herein, the term "needle" refers to any elongated member having a sharpened tip for puncturing or piercing. The term "needle" is not limited to traditional venipuncture needles, which are typically made of stainless steel and are relatively small in diameter. Although the term "needle" includes such venipuncture needles, it also includes piercing members made from other materials, such as plastic, and includes cannulas, coupling devices and the like.

Turning now to the drawings, FIG. 1 shows an exemplary disposable tubing and container set 10 for collecting blood from a donor 11. The illustrated disposable set may include a needle, such as a venipuncture needle 12, and a plastic tubing segment 16 attached to needle 12 and extending from needle 12 to a plastic, blood collection container 18. Although not shown in FIG. 1, needle 12 may be attached to one end of a needle hub and tubing 16 is attached to the other end of a needle hub (as shown, for example, in FIG. 2).

The disposable blood processing set may include a single blood collection container 18, or more commonly, as shown in FIG. 1, may include a primary container and additional, integrally attached containers 20 and 22, as is well known in the field. The methods and disposable sets for practicing such methods are well known and will not be discussed here. They are described in U.S. Pat. Nos. 4,222,379, 5,445,629 and 6,387,086, all of which are incorporated by reference herein. As noted above, however, the needle protector of the present invention is not limited to use with such blood collection kits, but may also be used in connection with other apparatus and methods used in the processing, treatment and collection of blood or other biological fluid.

Also, shown in FIG. 1 is a needle protector 40 embodying the present invention. As shown in FIG. 1, needle protector 40 is placed on or otherwise associated with tubing 16, which leads from the venipuncture needle to one or more collection containers. More specifically, needle protector 40 provides a sleeve that is relatively moveable with tubing 16, as described in more detail below.

Turning now to FIG. 2, there is shown a needle protector 40 which includes a body 42 having an open distal end 44 and open proximal end 46 (best seen in FIG. 5). Open distal and proximal ends 44 and 46, respectively, are adapted and sized to receive tubing 16 of the blood tubing set 10. As shown, for example, in FIG. 2, distal end 44 includes a larger opening adapted for and of sufficient size to receive the needle hub 20. On the other hand, open proximal end 46 is sized so that hub 20 cannot exit through the proximal end 46. As shown in FIG. 5, open proximal end 46 may include a multi-profile window, including a portion 47 having a smaller diameter and a portion 49 having a larger diameter. The multi-profile window is discussed in greater detail below.

Returning now to FIGS. 2 and 3, needle protector 40, and specifically body 42, includes a plurality of side walls 48, 50, 52 and 54. The outer surfaces of side walls define a needle protector body 42 with a generally rectangular shape. The inner surfaces of side walls 48, 50, 52 and 54 define an interior chamber 56 (FIG. 3) for receiving the needle assembly (i.e. needle 12, hub 20 and tubing 16). Of course, needle protector 40 can have any shape including, but not limited to, a cylindrical tube shape defined, for example, by a continuous arcuate wall.

As further seen in FIGS. 2 and 3, needle protector 40 may include retaining member 60 and a viewing slot 62. Preferably, retaining member 60 and viewing slot 62 are formed in top wall 48 near the proximal end 46 of needle protector 40.

Needle protector 40 may further include a outwardly extending flange 58 at the open distal end 44 of needle protector 40. Outwardly extending flange 58 allows the needle protector 40 to be locked inside a sampling tube holder, as shown and described in U.S. patent application Ser. No. 09/442,210, filed Nov. 17, 1999, incorporated by reference herein.

Turning now to FIGS. 4, 6, 7 and 8, needle protector 40 may also include guiding ledges 68 and 70. Guiding ledges 68 and 70 may be provided as outwardly extending lips that protrude from side walls 50 and 52 and/or depend downwardly from top wall 48. Guiding ledges 68 and 70 may span the entire length of the needle protector 40 from distal end 44 to proximal end 46. At the minimum, guiding ledges 68 and 70 may extend from distal end 44 substantially up to the proximal tip of retaining member 60. Guiding ledges 68 and 70 "guide" needle hub 20 as it is being retracted into needle protector 40 and prevent hub 20 from rotating once inside the needle protector 40.

As further shown in FIGS. 4 and 8, needle protector 40 may include a longitudinal groove 72 in one of the side walls of the needle protector 40. Preferably, groove 72 extends substantially the entire length (from distal end 44 to proximal end 46) and is formed in bottom wall 54 of needle protector 40. In the event that hub 20 has been inverted 180° as it enters protector 40), groove 72 is provided to receive and accommodate rib 22 of hub 20. Groove 72 allows hub 20 to be retracted, even in the inverted position, into needle protector 40, without interference from guiding ledges 68 and 70.

It will be appreciated that the locations of guiding ledges of 68 and 70 and groove 72 may be inverted. For example, guiding ledges 68 and 70 may extend externally from side walls 50 and 52, but at a location closer to bottom wall 54. Conversely, groove 72 may be formed in top wall 48.

Turning now to FIG. 6, there is shown a needle protector assembly including a needle hub 20, a needle 12, (and a length of tubing extending from the one end of hub 20) fully retracted into needle protector 40. As shown in FIG. 6, retraction of hub 20 beyond retaining member 60 provides a locked and secured needle within needle protector 40. Full and complete retraction of the needle hub into the locked position is evidenced by an audible "click" sound caused by the snapping of retaining member 60 as hub 20 clears the proximal tip end 61 of retaining member 60. Retaining member 60 is sufficiently flexible and resilient such that it will not restrict movement of hub 20 in the direction of the proximal end 46 during retraction. Retaining member 60 may be a detent that extends downwardly from side wall 48 into interior chamber 56 in the direction of proximal end 46. Retaining member 60 may depend downwardly at an angle relative to sidewall 48. Retaining member 60 acts as a catch and prevents movement of hub 20 back out through open distal end 44. Whether the needle hub has been securely locked can also be ascertained by visual observation through viewing slot 62.

Turning now to FIG. 5, a multi-profile window in open proximal end 46 is provided to receive and retain tubing 16 of the blood tubing set 10. The multi-profile window allows for easy threading of tubing 16 through needle protector 40 during assembly of the kit. It also provides a means for more firmly holding the tubing when necessary. For example, when threading the tubing during assembly or when retracting the needle assembly into needle protector 40 after donation, the larger profile 49 provides sufficient space to allow for easy retraction or movement of the tubing relative to needle protector 40. The smaller profile window 47 may be used to secure the tubing and substantially prevent relative movement of the needle assembly and protector 40 during, for example, manufacture, shipping and/or blood donation. Specifically, tubing 16 may be press-fit into the smaller profile window 47 to prevent relative movement of the tubing and protector 40. Of course, during blood donation, relative movement of needle protector 40 and tube 16 may also be achieved by simply taping tubing 16 to the arm of the donor.

Needle protector 40 is preferably a unitary needle protector. By "unitary," it is meant that needle protector 40 is made of a single piece construction and is not made up of two or more joined or separable parts. Needle protector may be made by casting, or more preferably, injection molding, or by other means that will be known to those of skill in the art. Needle protector 40 may be made of any material that is suitably rigid and puncture resistant and suitable for use in the medical field. For example, needle protector 40 may be made of any thermoplastic material that can be sterilized by known sterilization techniques, including, but not limited to autoclaving, gamma radiation or electron beam radiation.

For example, needle protector 40 may be made of a polyolefin material, such as, most preferably, polypropylene. Other suitable materials may include polyethylene, such as high density polyethylene, polyacetal and polycarbonate. Of course, needle protector 40 may also be made of blends of two or more of the above-described materials. Preferably, the material used for needle protector 40 may be transparent to allow for viewing of the interior chamber of needle protector 40.

FIGS. 9 and 10 show the needle protector of the present invention including an end cap 80 attached to needle protector 40 at the distal end 44. Cap 80 may be attached to needle protector 40 by hinges attached to a sidewall of needle protector 40. In one embodiment, cap 80 may be attached to sidewall 48 (or 54). In another embodiment, cap 80 may be attached to either sidewall 50 or 52. Cap 80 may be attached to needle protector 40 and, specifically, sidewalls by a hinge (s) 82. Hinge 82 is preferably a living hinge which snaps cap 80 open or closed by a simple flick with a finger. This allows easy, one-handed operation of needle protector 40. Cap 80 may preferably be further provided with a lip 84. Lip 84 allows the technician to open and close cap 80 in the manner described above. Finally, cap 80 may also include gripping members 86 to provide some friction with the user's fingers when cap 80 is being closed.

Blood donation using a disposable processing set with the needle protector of the present invention begins with the technician disinfecting an area of the donor's arm. Needle 12 is then inserted into the vein at the disinfected area, with needle protector 40 slidably spaced from needle 12. While maintaining the needle in the inserted and correct position, the technician will slide needle protector 40 along tubing 16 toward needle 12 so as to partially enclose hub 20 within needle protector 40.

Typically, the technician will place a strip of adhesive tape over, for example, side wall 48 and adhere the ends of the tape to the donor's skin. This maintains needle protector 40 in place on the donor's arm during the blood donation. The technician may also, optionally, press tubing 16 into small profile window 47 or secure tube 16 to the donor's arm with tape, as previously described.

When donation is complete, the technician may withdraw needle 12 from the donor's arm by simply pulling tubing 16 with one hand while gently pressing down on needle protector 40 with the other hand. Needle 12 is retracted until needle hub 20 has passed retaining member 60 and a "click" is heard.

Once needle 12 has been firmly secured within protector 40, the technician will remove the tape and treat the punctured area of the donor's arm. The secured needle protector may, optionally, then be placed into a sampling tube holder, as described in U.S. patent application Ser. No. 09/442,210, previously incorporated by reference. Thus, needle protector 40 allows for smooth and easy retraction of the needle hub assembly from the donor when donation is completed, and minimizes the risk of accidental needle stick.

While the present invention has been described in connection with the foregoing embodiments, it is to be understood that the invention is not limited thereto, but is intended to include various modifications and equivalent arrangements thereto.

The invention claimed is:

1. A needle protector for use with a needle assembly that includes a piercing end, a hub and a plastic tube attached to the hub, said protector comprising:
   a body including proximal and distal open end;
   a plurality of side walls extending between the said proximal and distal open ends, said side walls defining an interior chamber, wherein said distal open end is adapted to receive the hub of a needle assembly;
   wherein said proximal open end is comprised of an end wall, said end wall defining an aperture sized that said hub cannot pass through said proximal open end, said aperture defining a multiple profile window including a first profile sized and shaped to slidably receive said tubing and a second profile sized and shaped to retain said tubing, said aperture being completely enclosed by said end wall such that said tubing is contained within said aperture;
   wherein at least one of said side walls includes a flexible retaining member adapted for contacting said hub of said needle assembly and spaced a sufficient distance from said distal end such that when said needle hub is in the fully retracted position said piercing end is completely contained within said interior chamber; and
   wherein one of said side walls further comprises a longitudinally extending depression in the interior surface of said one of said side walls thereby defining an internal groove extending axially from said first open distal end to said open proximal end.

2. The needle protector of claim 1 wherein said side wall opposite said side wall including said retaining member, defines said groove.

3. The needle protector of claim 1 wherein said body further comprises an outwardly extending radial flange at said open distal end.

4. The needle protector of claim 1 further comprising a cap associated with said open distal end.

5. The needle protector of claim 1 wherein one of said side walls defines a slot for viewing said interior chamber.

6. The needle protector of claim 1 comprising a unitary single piece body of a substantially transparent plastic material.

7. The needle protector of claim 1 wherein said multiple profile window includes a dual profile window consisting of a smaller cross section profile and a larger cross section profile.

8. The needle protector of claim 7 wherein the smaller cross section profile is sized to substantially retain said tubing.

9. The needle protector of claim 7 wherein the larger cross section profile is sized to allow for free movement of said tubing therethrough.

10. A needle protector assembly comprising a needle assembly, including a piercing end attached to one end of a hub and a length of tubing attached to the opposite end of said hub, said hub further comprising a rib extending outwardly therefrom;
   a body including proximal and distal open ends;
   a plurality of side walls extending between said proximal and distal open ends, said side walls defining an interior chamber, wherein said distal end is adapted to receive the hub of said needle assembly, wherein one of said side walls includes a flexible retaining member adapted for contacting said hub of said needle assembly and spaced a sufficient distance from the distal end such that when said needle hub is in the fully retracted position said piercing end is completely contained within said interior chamber and wherein another of said side walls further comprises a longitudinally extending depression in the interior surface of said one of said side walls thereby defining an internal groove extending axially from said first open distal end to said open proximal end; and
   wherein said proximal open end is comprised of an end wall, said end wall defining an aperture sized so that said hub cannot pass through said proximal open end, said aperture comprising a multiple profile window including a first profile sized and shaped to slidably receive said tubing and a second profile sized and shaped to retain said tubing, said aperture being completely enclosed by said end wall such that said tubing is contained within said aperture.

11. The needle protector of claim 10 wherein said proximal open end comprises a multiple profile window adapted to selectively slidably receive and retain said tubing.

12. The needle protector of claim 11 wherein said multiple profile window includes a dual profile window consisting of a smaller cross section profile and a larger cross section profile.

13. The needle protector of claim 12 wherein the smaller cross section profile is sized to substantially retain said tubing.

14. The needle protector of claim 12 wherein the larger cross section profile is sized to allow for free movement of said tubing therethrough.

15. The needle protector of claim 10 wherein one of said side walls defines a slot for viewing said interior chamber.

16. The needle protector of claim 10 wherein said side wall opposite said side wall including said retaining member, defines said groove.

17. The needle protector of claim 10 wherein said body further comprises an outwardly extending radial flange at said open distal end.

18. The needle protector of claim 10 further comprising a cap associated with said open distal end.

19. The needle protector of claim 10 comprising a unitary body comprised of a substantially transparent plastic material.

* * * * *